US008490752B2

(12) United States Patent  (10) Patent No.: US 8,490,752 B2
James et al.  (45) Date of Patent: Jul. 23, 2013

(54) ACCURATE FLUID VOLUME MEASUREMENT FOR THERMALLY EXPANDING FLUIDS

(75) Inventors: Denman H. James, Windsor, CT (US); Francis J. Parnin, Suffield, CT (US)

(73) Assignee: United Technologies Corporation, Hartford, CT (US)

( * ) Notice: Subject to any disclaimer, the term of this patent is extended or adjusted under 35 U.S.C. 154(b) by 1877 days.

(21) Appl. No.: 11/585,439

(22) Filed: Oct. 24, 2006

(65) Prior Publication Data

US 2008/0093173 A1    Apr. 24, 2008

(51) Int. Cl.
*F01D 25/18*    (2006.01)

(52) U.S. Cl.
USPC ......................................................... 184/6.11

(58) Field of Classification Search
USPC ..................................................... 184/6.11, 6
See application file for complete search history.

(56) References Cited

U.S. PATENT DOCUMENTS

| 5,273,134 A | 12/1993 | Hegemier et al. |
| 5,402,110 A | 3/1995 | Oliver et al. |
| 6,481,978 B2 * | 11/2002 | Zamalis et al. ............... 417/228 |
| 6,577,959 B1 | 6/2003 | Chajec et al. |
| 2006/0054406 A1 * | 3/2006 | Delaloye ..................... 184/6.11 |
| 2006/0081419 A1 * | 4/2006 | Care et al. ................... 184/6.11 |
| 2006/0249332 A1 * | 11/2006 | Bruce .......................... 184/6.11 |
| 2007/0169997 A1 * | 7/2007 | Delaloye ..................... 184/6.11 |

FOREIGN PATENT DOCUMENTS

EP    1389671 A2    2/2004

OTHER PUBLICATIONS

Eugene A. Avallone and Theodore Baumeister III, Editors, Marks' Standard Handbook for Mechanical Engineers, 1996, McGraw-Hill, 10th Edition, Chapter 4.*
Evert W. Johnson, Forest Sampling Desk Reference, CRC Press 2000, Chapter 5.*
The extended European Search Report dated Oct. 27, 2011, in counterpart Application No. 07252957.1.

* cited by examiner

*Primary Examiner* — Michael Mansen
*Assistant Examiner* — Robert T Reese
(74) *Attorney, Agent, or Firm* — Kinney & Lange, P.A.

(57) ABSTRACT

A method for determining volumes of working fluids used in fluid operated systems that would be present at selected temperatures in working fluid reservoirs provided in those fluid operated systems based on measured volumes of the working fluids present in the reservoirs at measured temperatures, systems volumes and densities of the working fluids at the selected and measured temperatures.

20 Claims, 3 Drawing Sheets

ACCURATE FLUID VOLUME MEASUREMENT FOR THERMALLY EXPANDING FLUIDS

This invention was made with Government support under N00019-02-C-3003 awarded by the United States Navy and F33657-99-D-2051-0011 awarded by the United States Air Force. The Government has certain rights in this invention.

BACKGROUND OF THE INVENTION

The present invention relates to fluid operated systems using liquids as the working fluids in those systems such as hydraulic forcing systems and engine lubricating systems and, more particularly, to gas turbine engines such as turbofan engines and associated integrated drive generator lubrication systems.

Lubrication systems for turbine engines, such as a turbofan engine, and for associated equipment, such as an integrated drive generator, provide pressurized lubricant, an oil, to lubricate, cool and clean the engine main bearings, gear box gears, seals, and the like, and again for the lubrication of bearings and other parts in equipment associated with such turbine engines. During such lubrications, leakages past seals, and heating of the lubricating oil caused to occur due to mechanical energy losses in the lubricated apparatus that leads to evaporation, together result in lubricating oil losses during engine operations.

Such losses, even with a lubrication system oil reservoir, or reservoirs, for storing additional oil being continually kept available to the system, must be countered by adding further replacement oil at appropriate times to that reservoir or reservoirs. Thus, the remaining volume of the oil in the lubricating system after use of the corresponding engine or other equipment lubricated by the system is required to be monitored to determine the times at which additional oil must be added to the reservoir. Similarly, losses of hydraulic fluid, or leaks into the system, occur during operations of hydraulic systems thus also requiring the monitoring of the remaining volume of hydraulic fluid as the basis for replenishing same as needed.

Although seemingly such monitoring can be accomplished by simply noting the level of oil or hydraulic fluid in the corresponding reservoir, thermal expansion of the lubricating oil or fluid due to the heating thereof causes significant variations in the levels thereof at different temperatures as those levels are measured in those reservoir or reservoirs for a given actual mass of such oil or fluid in the system because the volume of that oil or fluid depends on its temperature. This dependence makes the determination difficult as to just what the current volume of oil is in a lubricating system by just measuring the volume in the reservoir, typically done through just measuring the depth of the oil therein. The same situation also typically arises in hydraulic systems. Thus, there is a desire to provide a method of accurately determining the current amount of a working fluid present in a working fluid operated system relative to the desired amount, i.e., for example, the amount of lubricating oil present in an turbofan engine lubricating system versus its initial fill amount, and to do so through a conveniently performed volume measurement which can be done at whatever the temperature is of that working fluid at the time of making that measurement.

BRIEF SUMMARY OF THE INVENTION

The present invention provides a method for determining amounts of working fluids present in fluid operated systems at selected temperatures based on measured volumes of the working fluids present in the reservoir or reservoirs provided in those fluid operated systems at measured fluid temperatures in the systems. Such fluid operated systems have working fluid use sites that are interconnected by passageways to form a working fluid distribution system therein having an entry connection from a corresponding working fluid reservoir or reservoirs from which working fluid in the reservoir enters the working fluid distribution system during operation of the fluid operated system. A return coupling from the working fluid distribution system to the reservoir or reservoirs from which the working fluid in the working fluid distribution system was distributed allows the working fluid in the distribution systems to return to this reservoir or these reservoirs during operation of the fluid operated system.

The method comprises predetermining the volume contained within the sites and passageways of the working fluid distribution system, the entry connection and the return coupling that together form a distribution system volume at a reference point in time, including the values of the variable volumes in some of the segments of the distribution system at that time, and measuring, or in a temperature equilibrium situation simply recording, the selected representative temperature at that time. At a subsequent selected time, measuring the current temperatures of the working fluid in those system segments and the values of the current variable volumes in some of the segments of the distribution system must be done to determine its measured current representative working fluid temperature, and the current volume or volumes of the working fluid in the reservoir or reservoirs, and the measured temperature or temperatures thereof, must also be determined to provide the currently measured working fluid volume. Determining the densities expected for the working fluid at the selected representative temperature and at the measured current representative temperature is accomplished by using a predetermined relationship between the fluid density and temperature. Calculating the volume of the working fluid that would be currently in the reservoir if it were currently at the selected representative temperature is completed with the values of the foregoing currently measured parameters.

DETAILED DESCRIPTION

Figure 1:
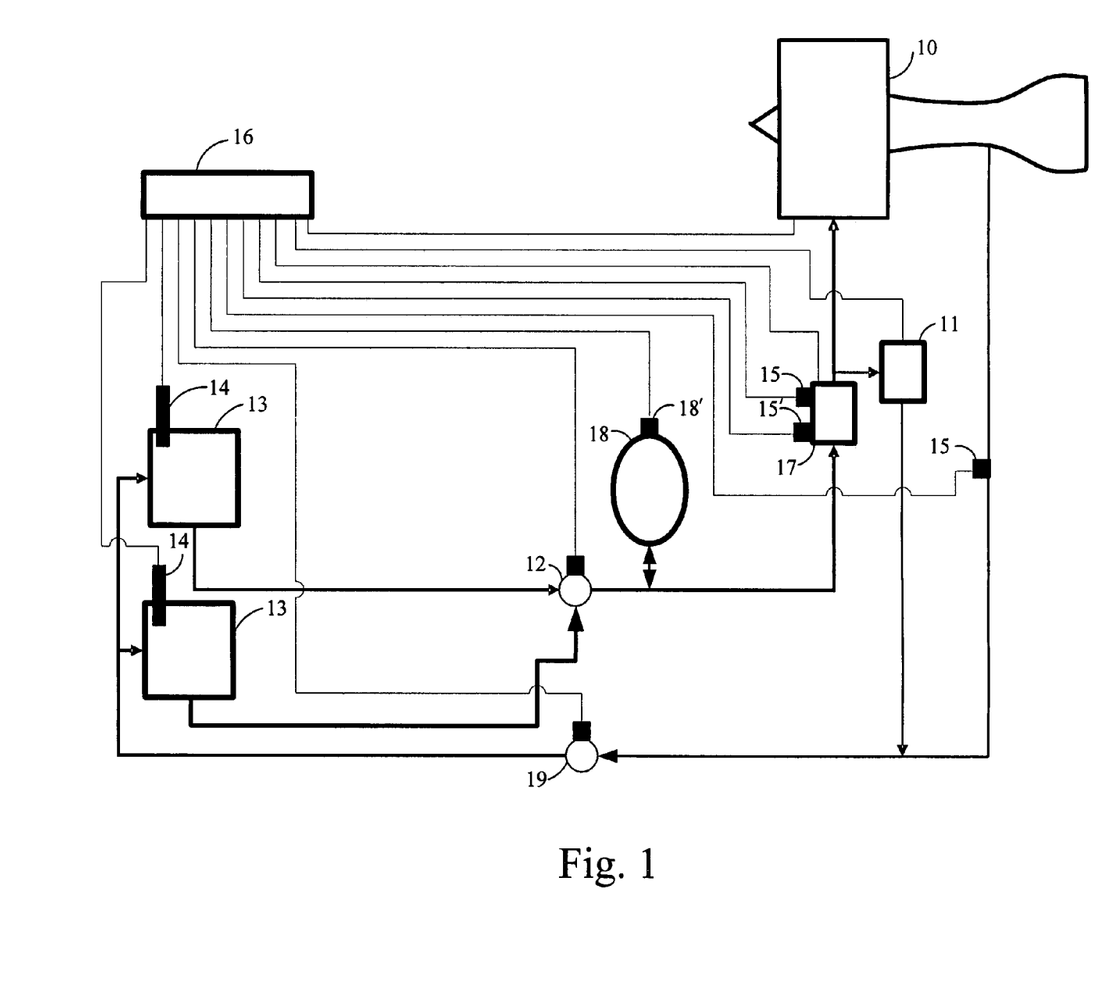
FIG. 1 shows a schematic diagram of an example of a working fluid operated system embodying the present invention.

FIG. 1 shows a schematic diagram representation of a jet engine, 10, such as a turbofan engine, as an example of a working fluid operated system on which the method of the present invention is practiced, this working fluid operated system being the engine and associated equipment lubrication system or systems. In jet engine 10, typically, a lubrication system is used to provide cooled, filtered lubrication oil to the internal components of a jet engine, typically bearings, gears and seals. This lubrication system may provide cooling and lubrication to other components, 11, that are not directly a part of the main engine but, perhaps, are subject to operating forces therefrom that power those components during their operation such as associated integrated drive generator systems that have their lubrication systems integrated with the engine lubrication system.

The lubrication system is shown in FIG. 1 as a typical example of such lubrication systems of which there are many variations. The FIG. 1 lubrication system example has a lubrication supply pump, 12, in the oil distribution and use system, or the operating system, which draws lubricant, or oil, from an oil supply reservoir or reservoirs, 13, that is then forced through the remainder of the oil distribution and use system, that is, forced through the oil distribution passageways to reach the oil use locations therein. The oil levels in reservoir or reservoirs 13 are monitored for oil temperature and oil levels through a corresponding oil temperature and reservoir oil level sensor, 14, with a corresponding one of these sensors being provided for each reservoir 13. Temperature sensors, 15, may be required in other segments of the oil distribution and use system to measure oil temperatures corresponding to the locations of those segments therein to provide data for use in determining a representative oil temperature for the oil distribution and use system. Similarly, pressure sensors, 15', measure oil pressure at suitable locations in the distribution and use system, and which also serve as volume sensors where used with variable volume elements having variable volume values typically dependent on the oil pressure thereat.

The data obtained from these measurements are transmitted by, or from, these sensors to an onboard data processing and control computer, 16, for processing of that using the methods of the present invention. In addition, computer 16 controls the operation of engine 10, selected ones of any of the other associated components 11, and various ones of the components of the lubrication distribution and use system such as lubrication supply pump 12. Alternatively, computer 16 could provide the data processing for this lubrication system and another computer could be provided to perform control of this system, or computer 16 could provide data processing and control for this lubrication system with another computer providing those services for engine 10.

The oil pumped by lubrication supply pump 12 through passageways in the distribution and use systems also goes to oil conditioning devices, 17, for cooling and filtering of which some are or may be controlled in their operations by computer 16. The temperature and pressure of the oil flowing in this conditioning equipment is measured, typically, by those of sensors 15 and 15' located in different system segments having such equipment therein as needed prior to, and over, system operating times, and the data so obtained is transmitted to onboard computer 16. Temperatures of the oil may differ in differing segments of the distribution and use systems, including those with oil conditioning devices 17, such as between adjacent system segments because of cooling devices being provided in some segments but not in others, and because of differing heat losses occurring in differing system segments, etc.

The distribution and use system may incorporate variable volume devices in different segments thereof at various locations in the lubrication system such as an accumulator, 18, which provides a variable volume that can be added to the system for safety against excessive oil pressure or for other purposes. All accumulators 18 of variable volume use a corresponding volume sensor, 18', to obtain their current volume addition to the system segment in which each is located as needed prior to, and over, system operating times, and to transmit this data to onboard computer 16 unless that added volume is a function of other known operating parameters so that the current volumes added to the system thereby can be calculated by the computer without receiving directly measured volume data.

Thereafter, the oil is then forced through more operating system passageways from conditioning equipment 17 to engine 10 or to other devices 11 that may or may not be part of the main engine. The oil cools and lubricates the internal parts of the engine, or other devices, and is then drawn from the engine or other device by a scavenge pump, 19, under control of computer 16 to be returned through further system passageways to reservoir or reservoirs 13, thereby completing the oil flow circuit. The sum of the volumes of the distribution and use system, including the passageways, fluid conditioning devices 17, accumulators 18, and jet engine 10 is referred to as the distribution and use system, operating system, volume in the lubrication system, and does not include the volume or volumes of reservoir or reservoirs 13.

Figure 2A:
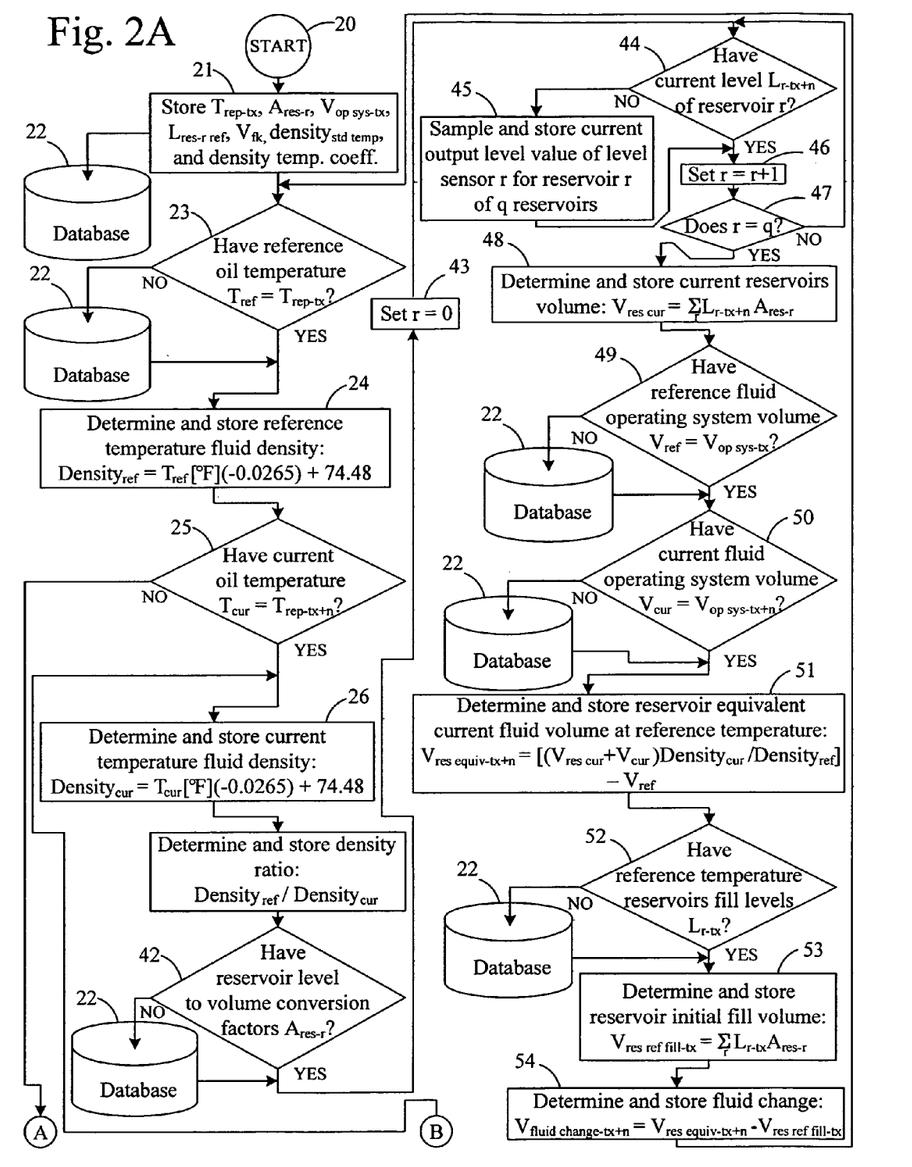
FIGS. 2A and 2B show a flow chart representing operations in the system of FIG. 1.

The operating sequence for computer 16 in the system of FIG. 1 is represented in FIG. 2A beginning in the upper left hand corner at a START balloon, 20. Preparatorily for the system operating sequence, relevant reference parameters for the lubrication system for jet engine 10 represented in FIG. 1 are stored by computer 16 through an action block, 21, by storing them in an associated computerized database, 22. The time dependant parameters stored are the representative temperature of the lubricant or oil in the system at some initial or reference time, $t_x$, designated $T_{rep-tx}$ and the volume of the operating system at that same time designated $V_{op\ sys-tx}$. The time independent parameters stored are a) the initial fill levels of the reservoir or reservoirs 13 in the system that are typically filled, or measured after a previous filling, at around time $t_x$ as corresponding initial reference values designated $L_{res-r\ ref}$ for each reservoir r, b) the effective oil surface areas at that level as corresponding initial reference values designated $A_{res-r}$ for each reservoir r, c) the fixed volume values $V_{fk}$ for the segments in the system, d) the density of the lubricant or oil at a standard temperature for the kind thereof chosen for use in the lubrication system designated density$_{std\ temp}$ and taken here as an example to be 74.48 lbs/ft$^3$, and e) the temperature coefficient of density for that kind of oil designated density temp. coeff. and taken here as an example to be $-0.0265$ lbs/ft$^3$/° F.

Next, either at, or at some convenient time past time $t_x$, or just prior to the selected beginning of a check on the volume of oil in the lubrication system at a later time $t_x+n$, computer 16 through a decision diamond, 23, gets the reference temperature of the oil in the lubrication system, $T_{ref}=T_{rep-tx}$, measured at time $t_x$ from database 22, and then determines what the density of the oil was at time $t_x$ as the initial reference density for that oil, Density$_{ref}$. This determination is made in a further action block, 24, using the density over temperature relationship of $$\text{Density}_{ref}=T_{ref}[°\ F.](-0.0265)+74.48$$

and the oil temperature $T_{ref}$ at time $t_x$ to provide that reference oil density with the result being stored in a local register of computer 16.

Similarly at the selected beginning of a subsequent check on the volume of oil in the lubrication system at a later time of some duration n of interest to the system user past the initial time $t_x$, computer 16, through a decision diamond, 25, gets the current representative temperature of the oil in the system, $T_{cur}=T_{rep-tx+n}$, at this later time $t_x+n$. Computer 16 then determines the density of the oil at time $t_x+n$ as the current density for that oil, Density$_{cur}$. This determination is made in another action block, 26, using the density over temperature relationship of $$\text{Density}_{cur}=T_{cur}[°\ F.](-0.0265)+74.48$$

and the current representative temperature of the oil in the system $T_{cur}$ to provide that current oil density with again the result being stored in a local register.

Figure 2B:
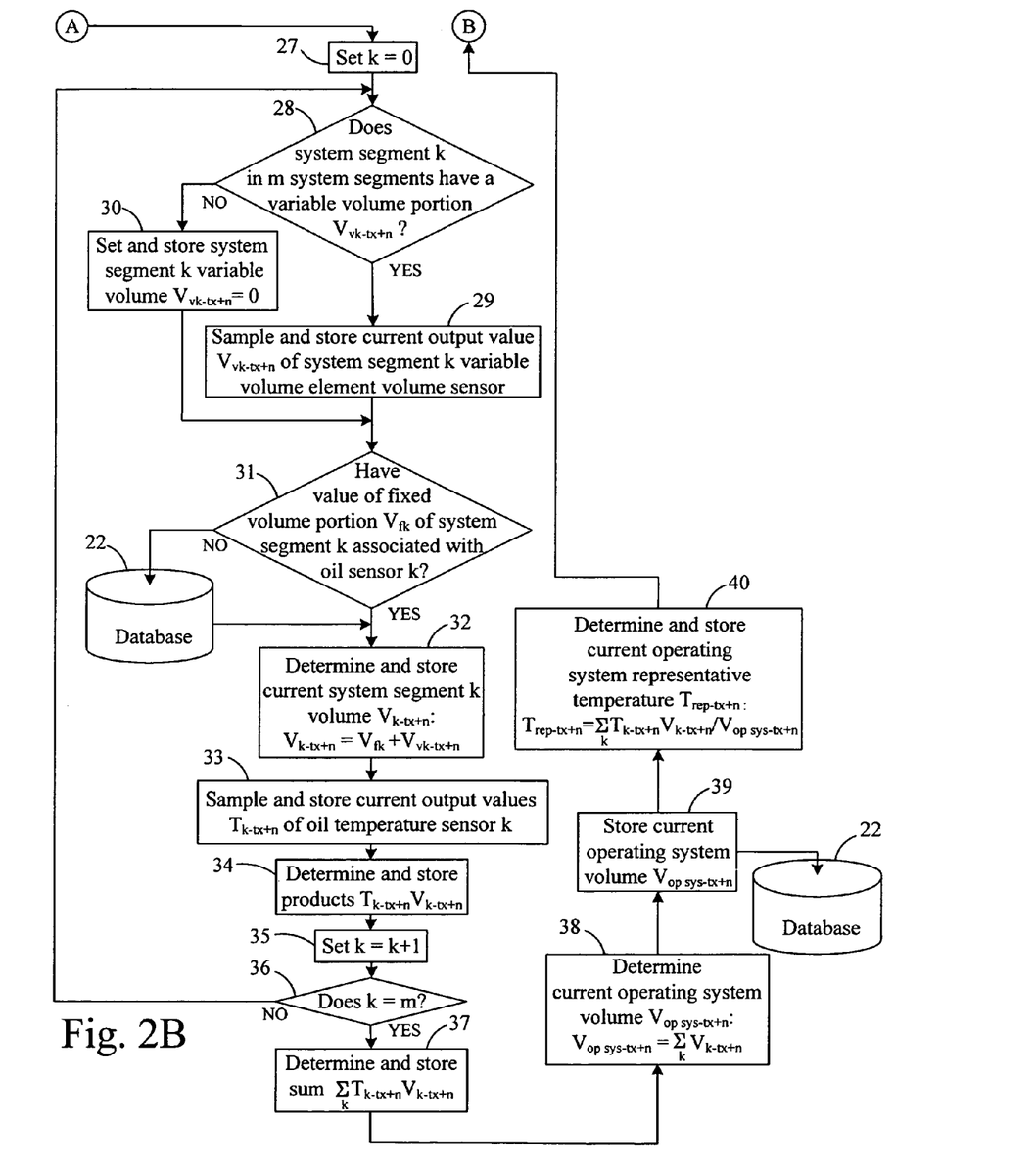

However, because temperatures of the oil may differ in differing segments of the distribution and use system, and because the volume may change in such differing segments, determining a representative current temperature for the oil can not be done accurately by just sampling measured temperatures from one or two of temperature sensors 15 and 15' at the current time. Instead, a careful determination must be made of such a temperature using a system volume segments based averaging process to determine that representative temperature prior to computer 16 entering action block 26 for use in that block, a determination process that is represented in FIG. 2B. Thus, FIG. 2B is reached out of decision diamond 25 through the balloons in FIGS. 2A and 2B labeled A prior to entering block 26 in the absence of computer 16 having that representative temperature $T_{rep-tx+n}$.

Computer 16 first sets count parameter k to zero in the computer segment counter therein in a first action block, 27, in FIG. 2B. Computer 16 then checks in a first decision diamond, 28, in FIG. 2B as to whether the first system segment k=0 has a variable volume portion of volume value $V_{vk-tx+n}$ or not. If so, computer 16 samples the output signal level of volume sensor 15', designated volume sensor k to correspond to that variable volume element, and stores in a local register the current variable volume value $V_{vk-tx+n}$ as measured by that volume sensor in a further action block, 29. If not, computer 16 sets the current output value $V_{vk-tx+n}$ to zero and stores that value in a local register in another action block, 30, which also results in computer 16 bypassing action block 29 since there is no volume sensor checking needed with respect to a system segment not having a variable volume portion.

After determining the variable volume of segment k=0, if any, computer 16 then checks in a further decision diamond, 31, as to whether it has or not the fixed volume value $V_{fk}$ for system segment k=0 as either a portion of, or as all of the volume of, that segment. If not, computer 16 gets the fixed volume value for segment k=0 from database 22. Thus, computer 16, now in possession of the fixed volume value $V_{fk}$ and of the current variable volume value $V_{vk-tx+n}$, adds them together to determine the current volume $V_{k-tx+n}$ of segment k=0 in an action block, 32, following decision diamond 31, or $$V_{k-tx+n} = V_{fk} + V_{vk-tx+n},$$

and then stores that value in a local register.

Having the current volume for segment k=0, the current temperature for that segment $T_{k-tx+n}$ is next found by computer 16 through its sampling the output signal of the temperature sensor 15 corresponding to that segment and storing that value in a local register as indicated in a further action block, 33. This provides the basis for computer 16 determining the product $T_{k-tx+n}V_{k-tx+n}$ for segment k=0 in another action block, 34, and storing the resulting value in a local register.

This completes the measurements and values determinations for segment k=0 so that computer 16 is then ready to complete the same measurements and value determinations for segment k=1, and then repeat the measurements and value determinations for all of the remaining segments in the m total number of segments, i.e. through segment k=m−1. This is accomplished by computer 16 incrementing the segment counter from the current value of k to k+1 in that computer in a corresponding action block, 35, and then checking to determine if the value of k has come to equal the number of system segments plus one, or m, in a decision diamond, 36. If not, computer 16 loops back to decision diamond 28 to provided the measurements and value determinations for the next segment, and continues to do so until the value of k=m.

Once the products $T_{k-tx+n}V_{k-tx+n}$ for each segment k have been determined and accumulated in a local register in computer 16, computer 16 moves from decision diamond 36 after finding that k=m to determine in a further action block, 37, a final sum thereof which is stored in the local register as $\Sigma T_{k-tx+n}V_{k-tx+n}$ representing a sum of the current values of the products over k for all of the segments k. Then computer 16 moves to another action block, 38, and sums the previously determined and locally stored segment current volumes $V_{k-tx+n}$ to determine a final sum thereof which is stored in a local register as $V_{op\,sys-tx+n} = \Sigma V_{k-tx+n}$ representing a sum of the current values of the segment volumes over k for all of the segments k to thereby provide the total current operating system volume $V_{op\,sys-tx+n}$. This volume is then also stored through a further action block, 39, in database 22 for a later call therefor by computer 16.

These measurements and value determinations for the operating system now completed allow computer 16 to determine the current representative temperature therefor, $T_{rep-tx+n}$, in the averaging process indicated above. Thus, computer 16 uses the values for the products and the operating system volume stored in local registers therein to determine this value in a final action block, 40, in FIG. 2B, or $$T_{rep-tx+n} = \sum_{k=0}^{m} T_{k-tx+n} V_{k-tx+n} / V_{op\,sys-tx+n}.$$

This value is then provided to action block 26 in FIG. 2A through the balloons in FIGS. 2A and 2B labeled B for the determination there of Density$_{cur}$ as described above. The completed, in block 26, determination and local storage of Density$_{cur}$, and the previously completed and locally stored determination of Density$_{ref}$ in block 24, allows the determination of the ratio Density$_{ref}$/Density$_{cur}$ in a succeeding action block, 41, in FIG. 2A.

Computer 16 then moves on to checks in a further decision diamond, 42, as to whether it has or not the previously stored reservoir to level volume conversion factors $A_{res-r}$ for each reservoir r in the q reservoirs in the lubrication system. If not, computer 16 gets the conversion factors from database 22.

With these conversion factors, computer 16 then needs the current levels of lubricant, or oil, in each reservoir r in the q reservoirs in the lubrication system to determine the volume or volumes of oil in that reservoir or reservoirs. Computer 16 first sets count parameter r to zero in the computer reservoir counter therein in a first action block, 43, in FIG. 2A. Computer 16 then checks in a first decision diamond, 44, in that figure as to whether it has the current level of oil in the first system reservoir r=0. If not, computer 16, in a further action block, 45, samples the output signal level of reservoir oil level sensor 14, which is designated level sensor r to correspond to that reservoir, and then stores in a local register the current reservoir level value $L_{r-tx+n}$ as measured by that level sensor.

This completes the measurement and value determination for segment r=0 so that computer 16 is then ready to complete the same measurement and value determination for reservoir r=1, and to then repeat the measurements and value determinations for all of the remaining segments in the q total number of segments, i.e. through segment r=q−1. This is accomplished by computer 16 incrementing the reservoir counter from the current value of r to r+1 in that computer in a corresponding action block, 46, and then checking to determine if the value of r has come to equal the number of system reservoirs plus one, or q, in a decision diamond, 47. If not, computer 16 loops back to decision diamond 44 to provide the measurement and value determination for the next reservoir, and continues to do so until the value of r=q.

Once the levels for each reservoir r have been found and accumulated in a local register in computer 16 along with the conversion factor corresponding thereto, computer 16 moves from decision diamond 47 after finding that r=q to determine in a further action block, 48, the products $L_{r-tx+n} A_{res-r}$ giving the volume of oil in each of corresponding reservoirs r. A sum of these products over r for all of the reservoirs, $\Sigma L_{r-tx+n} A_{res-r}$, is also formed as the current reservoirs oil volume, $V_{res\ cur}$, or $V_{res\ cur} = \Sigma L_{r-tx+n} A_{res-r}$, and stored in a local register as representing the current total volume of oil in all q of the reservoirs.

Next, through a decision diamond, 49, computer 16 gets the reference fluid or oil operating system volume $V_{ref} = V_{op\ sys-tx}$ from database 22, and then gets, through a further decision diamond, 50, the current fluid or oil operating system volume $V_{cur} = V_{op\ sys-tx+n}$ from database 22 where it was previously stored in action block 39 in FIG. 2B after the determination thereof in action block 38. Thus, computer 16, having in its local registers the density ratio Density$_{ref}$/Density$_{cur}$, the current reservoirs actual oil volume $V_{res\ cur}$, the operating system reference oil volume $V_{ref}$, and the operating system oil volume $V_{cur}$, can fin the equivalent current reservoir fluid or oil volume, $V_{res\ equiv-tx+n}$, at the reference temperature it would have had at the initial or reference time $t_x$. This determination is made in a further action block, 51, using the following expression $$V_{res\ equiv-tx+n} = [(V_{res\ cur} + V_{cur}) \text{Density}_{cur}/\text{Density}_{ref}] - V_{ref}$$

Computer 16 then gets the reference temperature reservoir or reservoirs initial or reference fill levels, $L_{r-tx}$, through a decision diamond, 52, from database 22 as the basis for determining the total initial or reference fill level, $V_{res\ ref fill-tx}$, for all of the q reservoirs together, or $V_{res\ ref fill-tx} = \Sigma L_{r-tx} A_{res-r}$. This is accomplished in a further action block, 53, and allows computer 16 to then determine the fluid change $V_{fluid\ change-tx+n}$ occurring in the lubrication system between the initial or reference time $t_x$ and the current volume check time $t_x+n$ as $V_{fluid\ change-tx+n} = V_{res\ equiv-tx+n} - V_{res\ ref fill-tx}$ in a further action block, 54. This value is stored for future review by, typically, engine and lubrication system maintenance people. Computer 16 then loops back to ahead of decision diamond 23 to be ready to make the next desired oil change determination relative to the initial, or reference, fill. However, computer 16 could alternatively loop back to ahead of action block 21 and enter there, as new reference parameters, the corresponding parameters found in this previous oil volume change determination to thereby allow the next change determination to be made relative to this previous determination.

A first sample calculation for a lubrication system which has a single reservoir and has a fixed operating system volume follows:

A jet engine 10 with a known operating system volume of 10 quarts begins operation with oil in the engine lubrication system at a temperature equal to 60° F. Oil level sensor 14 initially indicates that there are 12 quarts of oil in oil reservoir 13. After engine 10 operates for 10 minutes, the oil representative temperature reaches 220° F., and the oil level in reservoir 13 is now measured by sensor 14 to indicate that there is 13.3 quarts of oil therein. The density of the oil at 60° F. is 72.89 lb/ft$^3$ and at 220° F. the density is 68.65 lb/ft$^3$ leading, from the equations above, to $$V_{fluid\ change-tx+n} = ((13.3 + 10)/(72.89/68.65) - 10) - 12$$
$$= -0.06 \text{ quarts.}$$

Since the oil volume change is negative, that is, the oil volume is smaller after engine operation than the value prior thereto (which are both as a result of the calculation at the normalized temperature), the engine lubrication system is losing oil even though the oil level measured in the reservoir after engine operation is 13.3 quarts thus showing an increase in oil of 1.3 quarts.

A second sample calculation is for a lubrication system having two interconnected reservoirs 13 and an operating system of fixed volume is the following:

A jet engine 10 with a known operating system volume of 10 quarts begins operation having 12 quarts of oil measured by corresponding oil level sensors 14 in each of two reservoirs 13, this oil in the engine lubrication system being at a temperature equal to 60° F. After engine 10 operates for 10 minutes, the oil representative temperature reaches 220° F., and the two oil level sensors 14 on corresponding ones of oil reservoirs 13 in the connected system now measure oil levels indicating 13.3 and 13.0 quarts of oil in those reservoirs, respectively. The total volume of oil initially in the system prior to operating engine 10 is 24 quarts in the reservoirs, and 10 quarts in the operating system for a total of 34 quarts. The volume change result from the equations above is $$V_{fluid\ change-tx+n} = ((26.3 + 10)/(72.89/68.65) - 10) - 24$$
$$= 0.19 \text{ quarts.}$$

Since the oil volume change is positive, that is, the oil volume is larger after engine operation than the value prior thereto, that is, the oil volume has increased by 0.19 quarts, the engine lubrication system oil volume is increasing, and so indicates a possible leak of fluid from some source into the oil system.

A third sample calculation below is for a lubrication system having a single reservoir and an operating system of a fixed volume other than having an accumulator therein of a fixed volume which is filled from the main reservoir when the engine is operating:

A jet engine 10 with a known operating system volume of 10 quarts other than any addition thereto provided by the accumulator begins operation with that volume and with the oil in the engine lubrication system being at a temperature equal to 60° F. Oil level sensor 14 initially indicates that there are 12 quarts of oil in oil reservoir 13. After engine 10 operates for 10 minutes, the operating system increases the oil volume therein to 12 quarts because of the accumulator, and the oil representative temperature reaches 220° F. The oil level in reservoir 13 is now measured by sensor 14 to indicate that there are 9.8 quarts of oil therein. In this situation, the volume change result from the equations above is $$V_{fluid\ change-tx+n} = ((9.8 + 12)/(72.89/68.65) - 10) - 12$$
$$= -1.47 \text{ quarts.}$$

Since the oil volume change is negative, that is, the oil volume is smaller after engine operation than the value prior thereto to the extent of a decrease of 1.47 quarts, the system oil level is decreasing and so indicating a possible fluid loss.

A final sample calculation is again for a lubrication system having a single reservoir and an operating system of a fixed volume other than having an accumulator therein of a fixed volume which is filled from the main reservoir when the engine is operating:

A jet engine 10 with a known operating system volume of 10 quarts other than any addition thereto provided by the accumulator begins operation with that volume and with the oil in the engine lubrication system being at a temperature equal to 60° F. Oil level sensor 14 initially indicates that there are 12 quarts of oil in oil reservoir 13. After engine 10 operates for 10 minutes, the operating system increases the oil volume therein to 12 quarts because of the accumulator, but, for some reason, the oil representative temperature remains at 60° F. The oil level in reservoir 13 is now measured by sensor 14 to indicate that there are 10 quarts of oil therein. In this alternative situation, the volume change result from the equations above is $$V_{fluid\ change-tx+n} = ((10+12)/(1)-10)-12$$
$$= 0 \text{ quarts.}$$

Since the fluid temperature remains the same during operation for whatever reason, there is no oil density correction, and the change in measured level is compensated for by the change in system volume provided by the accumulator.

Although the present invention has been described with reference to preferred embodiments, workers skilled in the art will recognize that changes may be made in form and detail without departing from the spirit and scope of the invention.

The invention claimed is:

1. A method for determining volumes of lubricant used in a lubrication system of an aircraft turbofan engine that would be present at selected temperatures in the lubrication system based on measured volumes of the lubricant present in lubricant reservoirs provided in the lubrication system at measured temperatures of the lubricant, such the lubrication system further having lubricant use structures interconnected by passageways to which arrangement entry connections are made from each corresponding lubricant reservoir to allow lubricant in that reservoir to reach the lubricant use structures during operation of the lubrication system and from which arrangement return couplings are made to each corresponding lubricant reservoir to allow the lubricant to return to that reservoir during operation of the the lubrication system, the method comprising:

predetermining a fixed volume occurring within the lubricant use structures and passageways of the lubrication system, all entry connections, all return couplings together forming a distribution and use system of the lubrication system and further including in that distribution and use system any variable volume devices connected thereto so that any variable volume additions provided thereby are added to the fixed volume to predetermine a distribution and use system volume at a selected representative temperature;

measuring one or more subsequent temperatures of the lubricant at one or more locations in the lubrication system, and measuring any subsequent variable volume additions to the distribution and use system, to determine the subsequent measured representative temperature of the lubrication system;

measuring subsequent volumes of the lubricant in all lubricant reservoirs in the lubrication system to provide the subsequent measured lubricant volume;

determining densities expected for the lubricant at the selected representative temperature and at the subsequent measured representative temperature; and calculating the subsequent volume of the lubricant that would be in the lubricant reservoirs at the selected temperature as a calculated lubricant volume.

2. The method of claim 1 further comprising measuring the volume of lubricant supplied to fill the distribution and use system volume in the lubrication system at the selected representative temperature and also the volume of lubricant supplied to fill a selected portion of each of the lubricant reservoirs to provide together a reference lubricant volume, and comparing the calculated lubricant volume to the reference lubricant volume to determine a system lubricant loss difference therebetween.

3. The method of claim 1 wherein the calculating of the subsequent volume of the lubricant that would be in the reservoir at the selected temperature comprises adding the fixed volume and any subsequent variable volumes additions to determine the subsequent distribution and use system volume, adding the subsequent measured lubricant volume and the subsequent distribution and use system volume to form a sum that is multiplied by the density expected for the lubricant at the subsequent measured representative temperature to form a product that is divided by the density expected for the lubricant at the selected representative temperature to form a ratio, and subtracting from that ratio the distribution and use system volume.

4. The method of claim 1 further comprising determining the density ratio of the lubricant density expected at the selected representative temperature to the lubricant density expected at the measured representative temperature.

5. The method of claim 1 wherein the determining of the densities expected for the lubricant at the selected representative temperature and at the measured representative temperature is based on a density value at a standard temperature adjusted by combining therewith a temperature dependent correction term.

6. The method of claim 1 wherein the calculating of the subsequent volume of the lubricant that would be in the reservoir at the selected temperature comprises determining a segmentation of the distribution and use system based on each segment selected having a significant lubricant temperature difference between it and adjacent segments, measuring the subsequent lubricant temperature in each of the segments along with any subsequent variable volumes additions to that segment to find the subsequent segment volume through adding together the fixed volume for that segment and any subsequent variable volumes additions measured for that segment, forming the segment product by multiplying together the subsequent lubricant temperature therein and the subsequent segment volume for that segment, summing the segment products to form a system product sum, dividing the system product sum by the subsequent distribution and use system volume, the latter found by adding together the subsequent segment volumes, to thereby determine the subsequent measured representative temperature.

7. The method of claim 3 further comprising measuring the volume of lubricant supplied to fill the distribution system volume in the lubrication system at the selected temperature and also the volume of the lubricant supplied to fill a selected portion of each of the lubricant reservoirs to provide together a reference lubricant volume, and comparing the calculated lubricant volume to the reference lubricant volume to determine a system lubricant loss difference therebetween.

8. The method of claim 4 wherein the calculating of the volume of the lubricant in the reservoir at the selected temperature comprises adding the fixed volume and any subsequent variable volumes additions to determine the subsequent distribution and use system volume and adding the subsequent measured lubricant volume and the subsequent distribution and use system volume to form a sum that is divided by the density ratio to form a further ratio, and subtracting from this latter ratio the distribution and use system volume.

9. The method of claim 6 wherein the calculating of the subsequent volume of the lubricant that would be in the reservoir at the selected temperature further comprises adding the subsequent measured lubricant volume and the subsequent distribution and use system volume to form a sum that is multiplied by the density expected for the lubricant at the subsequent measured representative temperature to form a product that is divided by the density expected for the lubricant at the selected representative temperature to form a ratio, and subtracting from that ratio the distribution and use system volume.

10. The method of claim 8 further comprising measuring the volume of lubricant supplied to fill the distribution system volume in the lubrication system at the selected temperature and also the volume of the lubricant supplied to fill a selected portion of each of the lubricant reservoirs to provide together a reference lubricant volume, and comparing the calculated lubricant volume to the reference lubricant volume to determine a system lubricant loss difference therebetween.

11. The method of claim 9 further comprising measuring the volume of lubricant supplied to fill the distribution system volume in the lubrication system at the selected temperature and also the volume of the lubricant supplied to fill a selected portion of each of the lubricant reservoirs to provide together a reference lubricant volume, and comparing the calculated lubricant volume to the reference lubricant volume to determine a system lubricant loss difference therebetween.

12. The method of claim 1, wherein the lubricant use structures comprise engine main bearings, engine gear box gears, and engine seals.

13. The method of claim 1, wherein the lubricant use structures comprise engine main bearings, engine gear box gears, engine seals, and components that are not directly part of the aircraft turbofan engine.

14. A method for determining volumes of lubricants used in lubricating systems for aircraft turbofan engine equipment that would be present at selected temperatures in such systems based on measured volumes of the lubricants present in reservoirs in those lubricating systems at measured temperatures of the lubricants, such lubricating systems further having lubricant use structures interconnected by passageways to which arrangement entry connections are made from each corresponding lubricant reservoir to allow lubricant in that reservoir to reach the lubricant use structures during operation of the aircraft turbofan engine equipment and from which arrangement return couplings are made to each corresponding lubricant reservoir to allow the lubricant to return to that reservoir during operation of the aircraft turbofan engine equipment, the method comprising:

predetermining a fixed volume occurring within the use structures and passageways of the lubricant distribution and use arrangement, all entry connections and all return couplings together forming a distribution and use system and further including in that system any variable volume devices connected thereto so that any variable volume additions provided thereby are added to the fixed volume to predetermine a distribution and use system volume at a selected representative temperature;

measuring one or more subsequent temperatures of the lubricant at one or more locations in the lubricating system, and measuring any subsequent variable volume additions to the distribution and use system, to determine the subsequent measured representative temperature of the lubricating system;

measuring subsequent volumes of the lubricant in all lubricant reservoirs in the lubricant distribution and use system to provide the subsequent measured lubricant volume;

determining densities expected for the lubricant at the selected temperature and at the subsequent measured temperature; and calculating the subsequent volume of the lubricant that would be in the lubricant reservoirs at the selected temperature as a calculated lubricant volume.

15. The method of claim 14 further comprising measuring both the volume of lubricant supplied to fill the lubricant distribution system volume in the aircraft turbofan engine equipment at the selected temperature and also the volume of the lubricant supplied to fill a selected portion of the reservoir to provide together a reference lubricant volume, and comparing the calculated lubricant volume to the reference lubricant volume to determine a loss difference therebetween.

16. The method of claim 14 wherein the calculating of the volume of the lubricant that would be in the reservoir at the selected temperature comprises adding the fixed volume and any subsequent variable volumes additions to determine the subsequent distribution and use system volume, adding the subsequent measured lubricant volume and the subsequent distribution and use system volume to form a sum that is multiplied by the density expected for the lubricant at the subsequent measured representative temperature to form a product that is divided by the density expected for the lubricant at the selected representative temperature to form a ratio, and subtracting from that ratio the distribution and use system volume.

17. The method of claim 14 wherein the determining of the densities expected for the lubricant at the selected temperature and at the measured temperature is based on a density value at a standard temperature adjusted by combining therewith a temperature dependent correction term.

18. The method of claim 14 wherein the calculating of the subsequent volume of the lubricant that would be in the reservoir at the selected temperature comprises determining a segmentation of the distribution and use system based on each segment selected having a significant lubricant temperature difference between it and adjacent segments, measuring the subsequent lubricant temperature in each of the segments along with any subsequent variable volumes additions to that segment to find the subsequent segment volume through adding together the fixed volume for that segment and any subsequent variable volumes additions measured for that segment, forming the segment product by multiplying together the subsequent lubricant temperature therein and the subsequent segment volume for that segment, summing the segment products to form a system product sum, dividing the system product sum by the subsequent distribution and use system volume, the latter found by adding together the subsequent segment volumes, to thereby determine the subsequent measured representative temperature.

19. The method of claim 16 further comprising measuring both the volume of lubricant supplied to fill the lubricant distribution system volume in the aircraft turbofan engine equipment at the selected temperature and also the volume of the lubricant supplied to fill a selected portion of the reservoir to provide together a reference lubricant volume, and comparing the calculated lubricant volume to the reference lubricant volume to determine a loss difference therebetween.

20. The method of claim 18 wherein the calculating of the subsequent volume of the lubricant that would be in the reservoir at the selected temperature further comprises adding the subsequent measured lubricant volume and the subsequent distribution and use system volume to form a sum that is multiplied by the density expected for the lubricant at the subsequent measured representative temperature to form a product that is divided by the density expected for the lubricant at the selected representative temperature to form a ratio, and subtracting from that ratio the distribution and use system volume.

* * * * *